United States Patent
Stewart

(10) Patent No.: US 8,765,449 B2
(45) Date of Patent: Jul. 1, 2014

(54) THREE STAGE, MULTIPLE PHASE ANAEROBIC DIGESTION SYSTEM AND METHOD

(75) Inventor: William C Stewart, Caldwell, ID (US)

(73) Assignee: Advanced Bio Energy Development LLC, Caldwell, ID (US)

(*) Notice: Subject to any disclaimer, the term of this patent is extended or adjusted under 35 U.S.C. 154(b) by 499 days.

(21) Appl. No.: 13/056,841

(22) PCT Filed: Jul. 31, 2009

(86) PCT No.: PCT/US2009/052433
§ 371 (c)(1),
(2), (4) Date: Jan. 31, 2011

(87) PCT Pub. No.: WO2010/014919
PCT Pub. Date: Feb. 4, 2010

(65) Prior Publication Data
US 2011/0136213 A1    Jun. 9, 2011

Related U.S. Application Data

(60) Provisional application No. 61/085,252, filed on Jul. 31, 2008.

(51) Int. Cl.
| | |
|---|---|
| C02F 3/34 | (2006.01) |
| C12M 1/00 | (2006.01) |
| C12M 3/00 | (2006.01) |
| B09C 1/10 | (2006.01) |
| C12P 1/00 | (2006.01) |
| C12M 1/12 | (2006.01) |

(52) U.S. Cl.
CPC ... B09C 1/10 (2013.01); C02F 3/34 (2013.01); C12P 1/00 (2013.01); C12M 25/18 (2013.01)
USPC ............. 435/262; 435/303.2; 435/290.1; 210/603; 210/615; 210/617; 210/252

(58) Field of Classification Search
CPC ...... C12M 41/34; C12M 41/14; C12M 23/08; C12M 23/04; C12M 23/10; C12M 21/02; B09C 1/10; C02F 3/34; C22B 3/18; C12P 1/00; C12P 3/00; C12P 7/6463; C12P 7/649; C12N 1/12; A01G 1/04; C05F 17/0205; C05F 17/0258; C05F 17/027; C05F 17/006
USPC ............ 435/262, 303.2, 262.5; 210/201, 202, 210/252, 259, 603, 612, 613, 615–617
See application file for complete search history.

(56) References Cited

U.S. PATENT DOCUMENTS 4,022,665 A    5/1977    Ghosh et al.
(Continued)

FOREIGN PATENT DOCUMENTS

JP        61054293        3/1986
(Continued)

OTHER PUBLICATIONS

Busch, et al., A New and Sound Technology for Biogas from Solid Waste and Biomass, Water Air Soil Pollut: Focus, DOI 10.1007/s11267-008-9195-5. Dated: Dec. 11, 2008.

(Continued)

*Primary Examiner* — Michael Hobbs
(74) *Attorney, Agent, or Firm* — Buchanan Nipper

(57) ABSTRACT

A three stage, multiple phase anaerobic digestion system and method designed to separate the biological phases, optimize microbial activity in each phase, and significantly increase system reliability and energy production. The system physically separates the biological phases of anaerobic digestion based on particle size, particle density, and solubility of metabolic products. The system allows a complex multi-phased biological system to develop without the need for excessive control or operator intervention.

19 Claims, 4 Drawing Sheets

(56) References Cited

U.S. PATENT DOCUMENTS

| | | | |
|---|---|---|---|
| 4,318,993 A * | 3/1982 | Ghosh et al. | 435/294.1 |
| 4,652,374 A | 3/1987 | Cohen | |
| 4,849,108 A * | 7/1989 | de Wilde et al. | 210/603 |
| 5,398,814 A | 3/1995 | Sime | |
| 5,500,123 A | 3/1996 | Srivastava | |
| 5,525,229 A | 6/1996 | Shih | |
| 5,529,692 A | 6/1996 | Kubler | |
| 5,630,942 A | 5/1997 | Steiner | |
| 5,670,047 A | 9/1997 | Burke | |
| 6,342,378 B1 | 1/2002 | Zhang | |
| 6,716,351 B2 | 4/2004 | Fassbender | |
| 6,921,485 B2 | 7/2005 | Kilian et al. | |
| 7,556,737 B2 | 7/2009 | Zhang | |
| 7,563,302 B2 | 7/2009 | Camisa | |
| 2002/0096471 A1 | 7/2002 | Miller, III | |
| 2002/0102673 A1 | 8/2002 | Zhang et al. | |
| 2003/0094410 A1* | 5/2003 | Fassbender | 210/603 |
| 2004/0016525 A1 | 1/2004 | Gervais | |
| 2004/0050777 A1 | 3/2004 | Khan | |
| 2005/0011829 A1* | 1/2005 | Dong et al. | 210/603 |
| 2006/0060526 A1 | 3/2006 | Binning et al. | |
| 2007/0158264 A1 | 7/2007 | Zhang | |
| 2008/0187976 A1 | 8/2008 | Gondhalekar et al. | |

FOREIGN PATENT DOCUMENTS

| | | |
|---|---|---|
| KR | 100356966 | 10/2002 |
| WO | WO 01/36340 | 5/2001 |
| WO | WO 2006/042551 | 4/2006 |
| WO | WO 2008/016999 | 2/2008 |
| WO | WO2010085893 | 8/2010 |

OTHER PUBLICATIONS

EPA—Biosolids Technology Fact Sheet—Multi-Stage Anaerobic Digestion. Dated: Sep. 2006.
Marsh, Focus on Anaerobic Digestion, Renewable Energy Focus. com. Dated: Dec. 31, 2008.
Wynn, UK Joins European Drive to Make Energy from Waste. Dated: Oct. 12, 2009.
Written Opinion, PCT/US2009/052433. Dated: Oct. 7, 2009.
International Search Report, PCT/US2009/052433. Dated: Oct. 7, 2009.
Gerardi, M.H., The Microbiology of Anaerobic Digesters. . 2003, Hoboken, NJ, : Wiley-Inteerscience. 177 pp.
Pohland, F.G., Anaerobic Treatment: Fundamental Concepts, Appications, and New Horizons, in Design of Anaerobic Processes for the Treatment of Industrial and Municipal Wastes, J.F.M.a.F.G. Pohland, Editor. 1992, Technomic Publishing Co.: Lancaster, PA. pp. 1-40.
Palmowski, L.M. and et al., Anaerobic Degradation of Organic Materials—Significance of the Substrate Surface Area. Wat. Sci. Tech., 2003. 47(12): p. 231-238.
Gomec, C.Y. and et al, The Role of pH in the Organic Material Solubilization of Domestic Sludge in Anaerobic Digestion. Wat. Sci.Tech., 2003. 48(3): p. 143-150.
Sanders, W.T.M., Anaerobic Hydrolysis: Mechanism, Assessment of the Hydrolysis Rate and Pitfalls, in Harmonisation of Anaerobic Biodegradation, Activity and Inhibition Assays, J. Leigthart and H. Nieman, Editors. 2002, European Commission Institute for Environment and Sustainability: Lago d'Orta, Italy. pp. 1-7.
Sanders, W.T.M. and et al, Anaerobic Hydrolysis Kinetics of Particulate Substrates. Wat. Sci. Tech., 2000. 41(3): p. 7-24.
Sanders, W.T.M. and et al., Hydrolysis kinetics of dissolved polymer substrates. Wat. Sci. Tech., 2002. 45(10): p. 99-104.
Yu, H.-Q. and et al., High-Rate Anaerobic Hydrolysis and Acidogenesis of Sewage Sludge in a Modified Upflow Reactor. Wat. Sci.Tech. , 2003. 48(4): p. 69-75.
Deublein, D. and A. Steinhauser, Biogas From Waste and Renewable Resources. 2008, Weinheim: Wiley-VCH. 443.
Khanal, S.K., Anaerobic Biotechnology for Bioenergy Production. 2008, Ames, IA: Wiley-Blackwell. 301.
Azbar, N. and R. Speece, Two-Phase, Two-Stage, and Single-Stage Anaerobic Process Comparison. J. Env. Eng., 2001. 127(3): p. 240-249.
Fox, P. and F.G. Pohland, Anaerobic Treatment Applications and Fundamentals: Substrate Specificity during phase Separation. Water Environment Research, 1994. 66(5): p. 716-724.
Walker, M. and et al, Use of a Hydraulic Flush Reactor in a Two-Stage Anaerobic Digestion Process for Biodegradable Municipal Waste. Env. Eng. Sci., 2009. 26(11): p. 1599-1606.
Ghosh, S., Pilot-Scale Demonstration of Two-Phase Anaerobic Digestion Activated Sludge. Wat. Sci. Tech., 1991.23 (Kyoto): p. 1179-1188.
Ghosh, S. and et al., Pilot- and Full-Scale Two-Phase Anaerobic Digestion of Municipal Sludge. Water Env. Res., 1995. 67(2): p. 206-214.
Ghosh, S., Improved Sludge Gasification by Two-Phase Anaerobic Digestion. J. Env. Eng., 1987. 113(6): p. 1265-1284.
Kim, J.K. and et al., Effects of Temperature and Hydraulic Retention Time on Anaerobic Digestion of Food Waste. J. Bioscience Bioeng., 2006. 102(4): p. 328-332.
Kim, J.K. and et al., Volumetric Scale-Up of a Three Stage Fermentation System for Food Waste Treatment. Bioresource Technology, 2008. 99: p. 4394-4399.
Diamantis, V. and et al., Upflow anaerobic clarification tank (UACT) to upgrade existing anaerobic effluents. Wat. Sci. Tech., 2009. 59(12): p. 2411-2419.
Speece, R. and et al., The Role of Process Configuration in the Performance of Anaerobic Systems. Wat. Sci. Tech., 1997. 36(6-7): p. 539-547.
Pohland, F. and S. Ghosh, Developments in the Anaerobic Stabilization of Orgasnic Wastes—The Two Phase Concept. Env. Lett., 1971. 1(4): p. 255-266.
Hartmann, H. and et al., Increase of Anaerobic Degradation of Particulate Organic Matter in Full-Scale Biogas Plants by Mechanical Maceration. Wat. Sci. Tech., 2000. 41(3): p. 145-153.
Cysbeiros, D. and et al., Anaerobic digestion of maize in coupled leach-bed and anaerobic filter reactors. Wat. Sci. Tech., 2008. 58(7): p. 1505-1511.
Kubler, H. and C. Schertler, Three-Phase Anaerobic Digestion of Organic Wastes. Wat. Sci. Tech., 1994. 30 (12): p. 367-374.
Park, C. and et al., Upgrading of Anaerobic Digestion by Incorporating Two Different Hydrolysis Processes. J. Biosci. Bioeng., 2005. 100(2): p. 164-167.
Climenhaga, M.A. and C.J. Banks, Uncoupling of Liquid and Solid Retention Times in Anaerobic Digestion of Catering Wastes. Wat. Sci. Tech., 2008. 58(8): p. 1581-1587.
Wang, J. and et al., A hybrid anaerobic solid—liquid system for food waste digestion. Wat. Sci. Tech., 2005. 52 (1-2): p. 223-228.
Wang, Z. and C. Banks, Evaluation of a two stage anaerobic digester for the treatment of mixed abattoir wastes. Process Biochem., 2003. 38: p. 1267-1273.

* cited by examiner

THREE STAGE, MULTIPLE PHASE ANAEROBIC DIGESTION SYSTEM AND METHOD

BACKGROUND OF THE INVENTION

Anaerobic digestion refers to both a natural microbial process, which takes place in the absence of oxygen, and, an engineered process, which utilizes the microbial process. Both produce methane gas ($CH_4$) as an end product. Anaerobic digestion is of great interest today due to its potential as a renewable energy source.

There is much confusion regarding the use of the terms "stage" and "phase" in the anaerobic digestion literature. Numerous authors have used the terms interchangeably. However, as used herein, the term "phase" is used to refer to biological steps in the anaerobic digestion process, whereas the term "stage" refers to an engineered physical entity (e.g., tank, container) used to contain the microbial phases.

The term "feedstock," also referred to as influent, refers to liquid and solid material fed into a an anaerobic digester, including but not limited to dairy manure/waste, municipal and industrial waste water sludge, organic material, biomass waste, biodiesel production waste, ethanol production waste, and food processing waste.

Anaerobic digestion is a complex process, mediated by a diverse array of microorganisms in the absence of oxygen. During anaerobic digestion, these microorganisms digest organic matter and produce methane gas as an end product. The complexity of the anaerobic microbial community is illustrated by data identifying over 9,000 active species in wastewater sludge digesters (Curtis (2002)).

Anaerobic digestion has been described as a three phase process (Geradi (2003)), a four phase process (Schink (1992); Deublein and Steinhauser (2008); Khanal (2008)), a five phase process (Liu and Ghosh (1997)), and a nine phase process (Pohland (1992)). These great variations in how the literature defines the number of phases present clearly indicates the complexity of the microbial systems involved.

Most recently, a four-phase process, constituting a food chain, has been generally accepted as a working model (Deublein and Steinhauser (2008); Khanal (2008)). These four phases consisting of a Hydrolysis Phase, an Acidogenesis Phase, an Acetogenic Phase, and a Methanogenesis Phase.

The Hydrolysis Phase is the first phase. The Hydrolysis Phase involves the digestion of complex carbohydrates, proteins and lipids into simpler substrates such as sugars, amino acids and fatty acids. It is analogous, in many ways, to the functions carried out by the stomach in mammalian digestive systems. Hydrolysis bacteria include both facultative anaerobic microorganisms (able to live under aerobic as well as anaerobic conditions) and strictly anaerobic microorganisms. Hydrolysis bacteria tend to be highly resistant to environmental fluctuations such as temperature and pH changes, thrive in an acidic environment, have high reproductive rates and growth rates, and are not usually adversely affected by toxins and heavy metals which may be present in the feedstock. Since the hydrolysis step is required to treat raw particulate matter, it often is a rate-limiting step in the anaerobic process due to the difficulty of digesting these often complex substrates (Sanders, et al. (2000); Zeeman and Sanders (2001); Sanders (2002); Gomec, et al. (2003); Gosh (1985)). Improved mixing and particulate disruption approaches can go far to minimizing this potential limiting problem (Sanders, et al. (2000); Palmowski, et al. (2003)), as has been shown in a recent report on the effect of optimizing sludge digester mixing (Marx, et al. (2007)).

The Acidogenesis Phase is the second phase in the anaerobic food chain. The Acidogenesis Phase involves another group of both facultative and strictly anaerobic bacteria that, utilizing the simple substrates provided by the hydrolysis bacteria, metabolize these secondary compounds into water soluble organic acids, alcohols, and carbon dioxide and hydrogen gas (Britz, et al. (1994); Yu, et al. (2003)). One study identified two hundred and eighty eight (288) different strains of acidogenic microbes in four anaerobic digesters in South Africa (Britz, et al. (1994)), illustrating the complexity of this phase.

The Acetogenic Phase is the third phase in the anaerobic food chain. In the Acetogenic Phase, homoacetogen bacteria utilize the products produced by the prior Acidogenesis Phase acidogens. The homoacetogen bacteria produce water-soluble acetate, an important precursor to methane formation (Deublein and Steinhauser (2008); Khanal (2008)).

The Methanogenesis Phase is the fourth and final phase. The Methanogenesis Phase results in the production of methane gas ($CH_4$). Methane producers are not true bacteria, but belong to an ancient group of microorganisms termed the Archaea. Recent evidence indicates that methanogens were active 3.5 billion years ago (Uneno, et al. (2006)). There are numerous species of methanogens capable of metabolizing a variety of low molecular weight water-soluble organics and gases. Methanogens are among the most strictly anaerobic organisms known, their growth being inhibited by the presence of even extremely small amounts of oxygen. Methanogens also are slow in reproducing, prefer a basic pH, and tend to be negatively affected by potential toxins such as heavy metals, solvents, pesticides and herbicides. Methanogens are also adversely affected by relatively small changes in environmental factors, such as pH and temperature. Most of the reputation of anaerobic digesters for instability, measured by the cessation of biogas production, can be traced to a failure of the methanogen populations.

The natural biological processes described above have been used extensively in an engineered application for over 100 years, long before the intricate biological relationships were understood. Said application has been almost exclusively at wastewater treatment plants for the stabilization and volume reduction of sludges. The production of energy has not been the primary goal of these systems. There are approximately 16,000 individual anaerobic digestion tanks operating in the United States alone. These tanks range in size from several hundred thousand gallons to several million gallons.

The vast majority are single stage systems where the four biological phases are forced to operate in a single tank. This creates numerous operational problems.

First, the hydrolysis bacteria and acidogenic bacteria (acidogens) have pH optimums of 5.5 to 6.5; whereas the methanogenic bacteria (methanogens) have pH optimums of 7.8 to 8.2 (Khanal, 2008). This presents challenges with using a single stage reactor (digestion tank) because hydrolysis begins immediately when the raw organic feedstock enters the digestion tank. Hydrolysis causes a rapid drop in pH as acidic products such as organic acids are rapidly produced. This acidic pH in turn inhibits the growth and metabolic activity of the methanogens.

To counteract this, a buffering agent (e.g., lime) must be added to the digestion tank to raise the pH to 7.8 to 8.5, the optimum pH for methane ($CH_4$) production. This pH adjustment must be estimated and performed manually because the quantity of buffering agent required will depend upon multiple factors, including, but not limited to, the feed rate and the chemical characteristics of the undigested organics in the feedstock. Due to the size of these reactors, substantial quantities of buffering agent are needed to adjust the pH. Since the hydrolysis phase is facilitated by acid conditions, raising the pH to satisfy the requirement of the methanogens can inhibit the rate of hydrolysis, making operation of the digester a precarious balancing act requiring trained and alert operators. No matter how skilled the operator is, effectively combining efficient digestion and energy production has been virtually impossible in such a conventional digester.

Second, methanogenic organisms are slow reproducers and do not compete well for attachment space with the more robust and aggressive hydrolysis and acidogenic populations.

Third, in order to achieve the higher temperatures favored by methanogens, the contents of the entire digestion tank must be heated via a heating means (e.g., heater) to 30° C. to 38° C. for mesophilic operation or 49° C. to 57° C. for thermophilic operation, at which latter temperature range the highest rates of methane ($CH_4$) production are achieved. Due to the large tank sizes typically used, these elevated temperatures require the utilization of significant amounts of energy (to heat the digestion tank), often reducing the net energy output of the anaerobic digestion system by as much as fifty percent (50%) or more.

Fourth, heavy metals or other toxins introduced into the single reactor with the feedstock come into immediate and direct contact with the environmentally sensitive methanogens. This is a frequent contributor to digester problems and reduction or cessation of methane ($CH_4$) production.

Fifth, each time digested solids are discharged from the single digestion tank, a portion of the valuable, but slowly reproducing, methanogens, which are attached to the solid particles, are also lost.

Sixth, methane gas ($CH_4$) produced by conventional anaerobic digesters has a high carbon dioxide ($CO_2$) content, often totaling 30 to 40 percent or more. For this reason, it has a lower BTU value than natural gas, and is referred to as "biogas." Carbon dioxide is a food source for methanogens, and thus the presence of $CO_2$ in the biogas is an indication of conversion inefficiency in single stage and two stage anaerobic digesters.

Seventh, these operational challenges require a highly trained and attentive operational staff to properly operate conventional digesters. Such staff is in short supply.

The above items are the main reason why anaerobic digestion has not progressed more widely as a reliable source of renewable energy.

In an attempt to solve these problems, various multiple stage reactor configurations, using two or more separate tanks, have been proposed. Two stage reactor designs attempt to isolate the hydrolysis/acidogenesis phase in the first tank, and the methanogenic phase in a second tank. This is based on the well-established fact that the food for the methanogens is water-soluble.

In addition, three-stage and even four-stage reactor configurations have been proposed. However, none of these have solved the operational sensitivity problems, nor have they significantly increased biogas yields or biogas purity as evidenced by the low numbers of full-scale multi-stage installations which have been constructed. Single stage digesters are still the norm.

As a potential source of renewable energy, anaerobic digestion has a number of distinct advantages over other biofuels, such as ethanol or biodiesel.

First, it produces energy from existing waste organics (e.g., animal manure, municipal solid waste, food processing waste, wastewater treatment sludge, process sludge from such industries as ethanol production, biodiesel production, and paper mills). There are enormous quantities of these waste organics readily available.

Second, in deriving energy from these waste organics, anaerobic digestion also performs a significant role in ground water protection, odor control, and greenhouse gas reduction.

Third, anaerobic digestion can be used to produce energy from biomass crops.

Fourth, anaerobic digestion does not require energy intensive drying prior to digestion.

Fifth, there is a large, albeit inefficient, pre-existing installed base of single stage digesters, for instance it has been estimated that there are 12,000 to 16,000 individual digester tanks in the United States and over 20,000 in Europe. This installed base provides engineering and operational expertise on construction, operation, safety and utilization issues for the produced methane gas ($CH_4$). Additionally, the installed base is ripe for retrofitting with technological enhancements aimed at increasing methane gas ($CH_4$) production.

SUMMARY OF THE DISCLOSURE

This disclosure describes a three stage, multiple phase anaerobic biotechnology process designed to (1) significantly simplify the operational requirements, (2) significantly increase the reliability, and (3) significantly increase the organic degradation and methane gas production rates. The ultimate design goal of this invention is to make anaerobic digestion a reliable and profitable source of methane gas as a renewable energy source.

DESCRIPTION OF THE PREFERRED EMBODIMENTS

Figure 1:
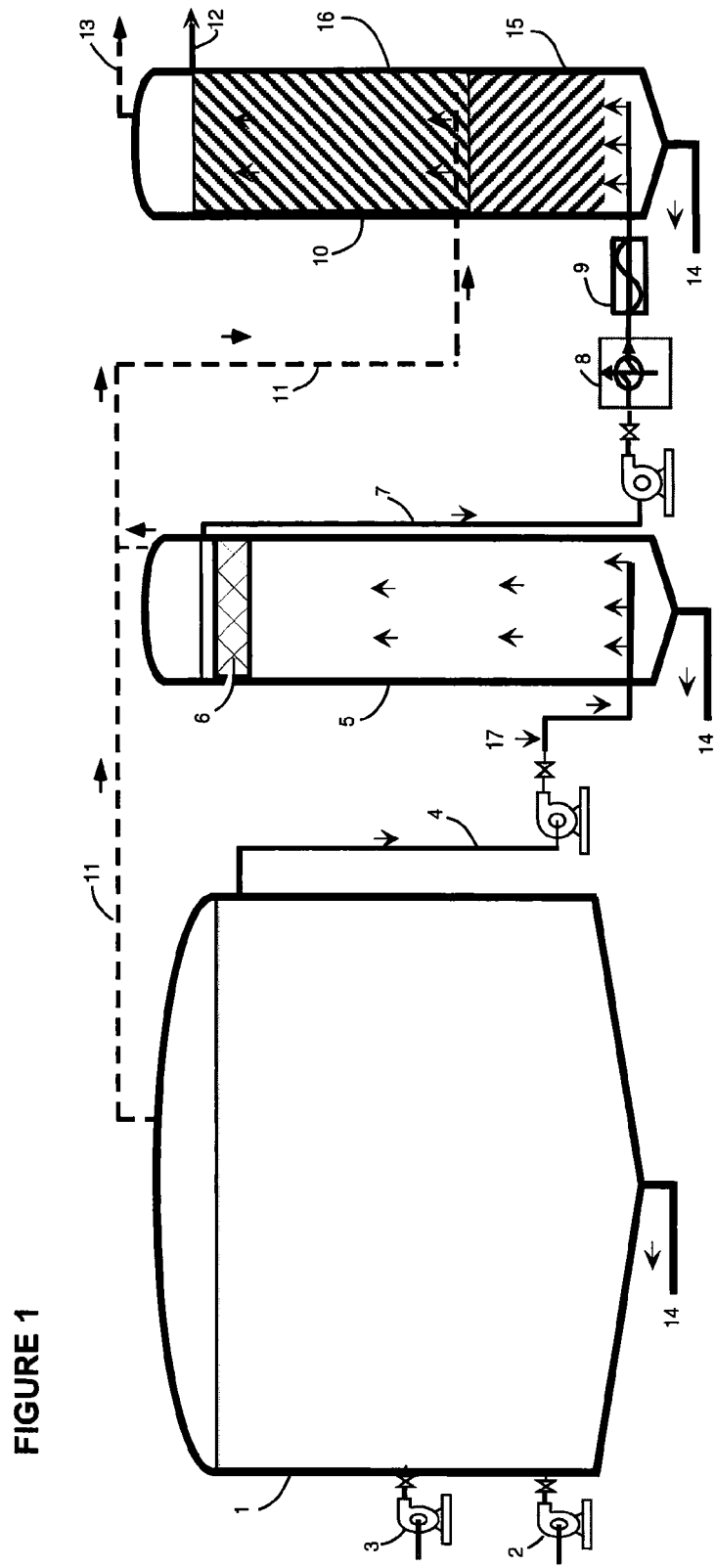
FIG. 1 is a schematic representation of one embodiment of a three stage, multiple phase anaerobic digestion system.

While the invention is susceptible to various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined herein.

In the following description and in the figures, like elements are identified with like reference numerals. The use of "e.g.," "etc," and "or" indicates non-exclusive alternatives without limitation unless otherwise noted. The use of "including" means "including, but not limited to," unless otherwise noted.

Disclosed is a three stage, multiple phase anaerobic digestion system and method. The preferred embodiment of the anaerobic digester is a three-stage process designed to separate the biological phases, optimize microbial activity in each phase, and significantly increase system reliability and energy production. The system physically separates the biological phases of anaerobic digestion based on particle size, particle density, and solubility of metabolic products. The system allows a complex multi-phased biological system to develop without the need for excessive control or operator intervention.

A schematic of the preferred embodiment of the anaerobic digester process is shown in FIG. 1. FIG. 1 showing the three stages (Stages I, II and III). Multiple systems could comprise each stage, for instance as shown in FIGS. 2A and 2B.

Figure 2A:
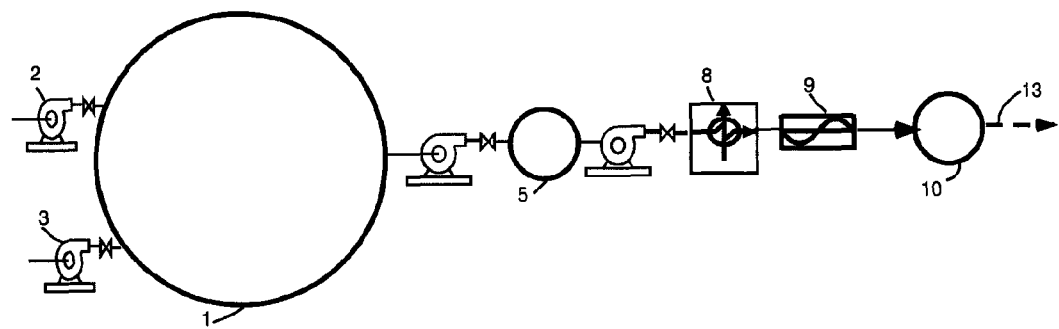
FIG. 2A is a schematic representation of a second embodiment of a three stage, multiple phase anaerobic digestion system.

FIG. 2A shows a second embodiment. FIG. 2A showing a single Stage I, a single Stage II, and a single Stage III, all in a series configuration. This type of implementation may be best for smaller systems.

Figure 2B:
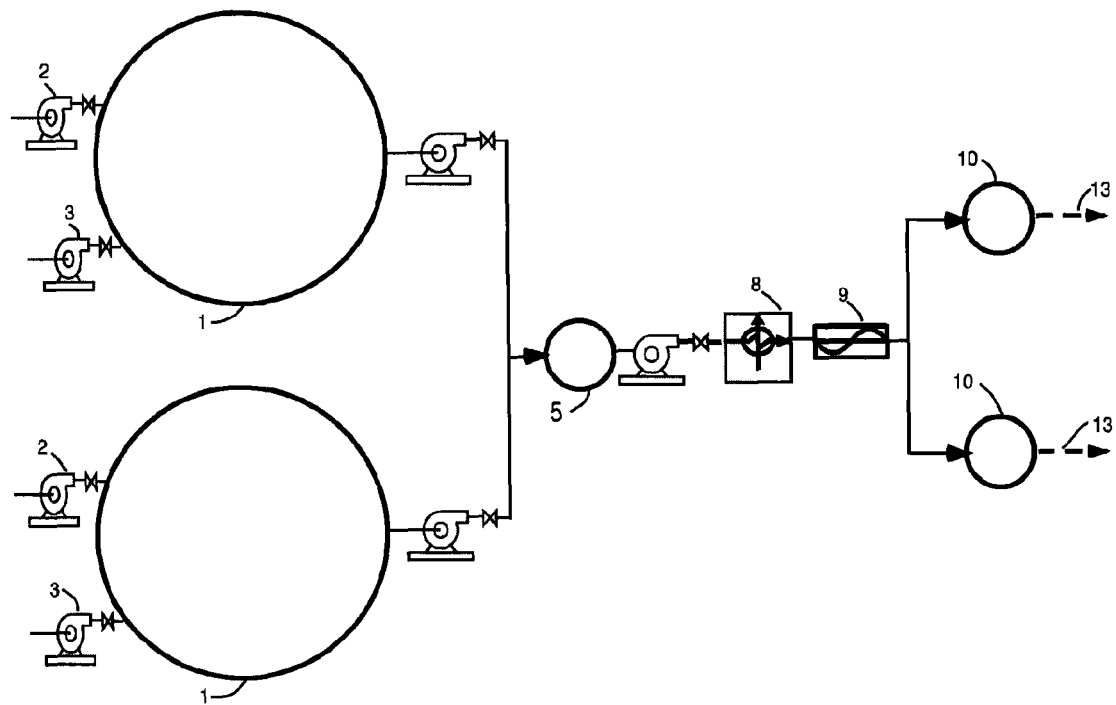
FIG. 2B is a schematic representation of a third embodiment of a three stage, multiple phase anaerobic digestion system.

FIG. 2B shows a third embodiment. FIG. 2B showing dual Stage I and Stage III, with a single Stage II. This embodiment is used with alternating mixing and feed from dual Stages I to single Stage II, and alternating feed from single Stage II to the dual Stage III's for larger systems.

Stage I takes place in the primary (first) digestion tank 1. It is preferably similar in size and configuration to that used in conventional single stage anaerobic digestion systems. Stage I is operated as a complete mix reactor wherein a feed pump 2 injects raw feedstock into the Stage I digestion tank 1. The primary digestion tank 1 is provided with at least one mixing means 3 (e.g., mechanical mixer, internal hydraulic jet nozzles, external chopper pumps) for mixing the contents of the primary digestion tank 1 and for causing rapid size reduction of the raw organic solids contained in the feedstock. This mixing and size reduction preferably uses the Liquid Dynamics Jetmix® systems.

Stage I is optimized for mechanical size reduction of the incoming organic solids and extensive but incomplete microbial hydrolysis. Stage I is operated with full power mixing interspersed with shorter settling periods of either quiescent operation (no mixing) or reduced power mixing. This is to allow the denser solids to settle while the less dense but still incompletely hydrolyzed suspended and colloidal solids and water soluble compounds are drawn off as supernatant from the upper surface of the Stage I digester at a liquid outlet and pumped through a lower (first) conduit 4 to Stage II at a second digestion tank inlet.

Unlike a conventional anaerobic digester, no pH adjustment or buffering agent is required in Stage I, allowing the prevailing acidic conditions (pH of 5.5 to 6.5) to increase the rate of particle disruption and hydrolysis. Since pH adjustment in Stage I is not required, influent feed rates of the feedstock and types of feedstocks can be varied without adversely affecting methane production, as would occur in a conventional digester.

Methane ($CH_4$) production in Stage I is suppressed by the dominance of the hydrolysis bacteria, the aggressive mixing, and the acidic pH. Gases produced in Stage I are primarily carbon dioxide ($CO_2$) and hydrogen ($H_2$). These gasses, collected at a first raw gas outlet, are piped to the Stage III reactor via a raw gas collection system (e.g., upper conduit 11) to be used as additional food for the methanogens in Stage III.

Toxins and heavy metals in the feedstock are retained in the Stage I reactor through chemical binding and bioremediation effects, and thus do not adversely impact the methanogens in Stage III. Digested sludge, which falls to the bottom of the Stage I tank due to increased density, is periodically removed via a drain 14. Digested sludge can also be periodically removed from the Stage II and/or Stage III tanks.

Since the activity of the methanogens is suppressed in Stage I, it is no longer necessary to operate the Stage I reactor at the elevated temperatures required to optimize methane production. The Stage I reactor can be heated to lower operating temperatures (preferably 24° C. to 34° C.) than that required for the methanogens. This increases net energy production of the overall system, particularly for thermophilic operation.

Figure 4:
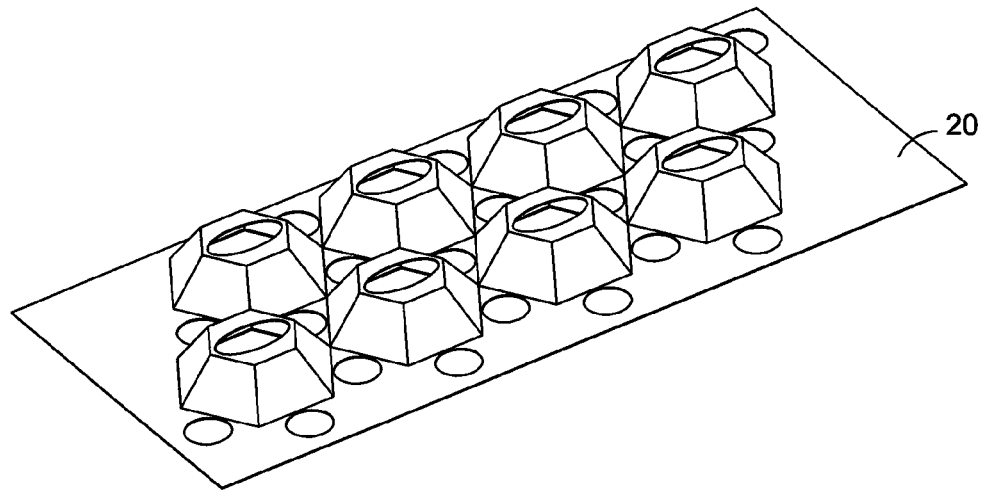
FIG. 4 is a perspective view of Applicant's proprietary horizontal plate microbial support media.
Figure 5:
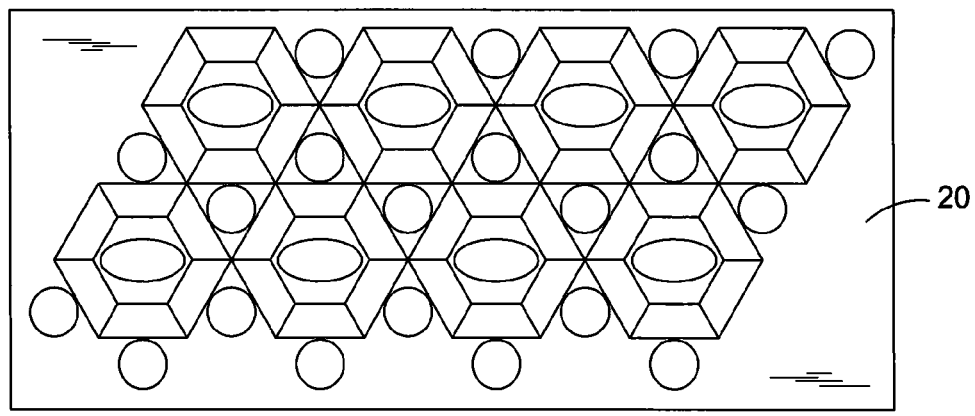
FIG. 5 is a plan view of Applicant's proprietary horizontal plate microbial support media.

Stage II takes place in the secondary (second) digestion tank 5 which is operated as an upflow fluidized bed reactor. The fluidized bed entraps the fine suspended and colloidal solids captured from the Stage I supernatant. The pH in the secondary digestion tank, like the primary digestion tank, being 5.5 to 6.5. Upflow velocity in Stage II is adjusted to that which will minimize overflow of the suspended solids to the Stage III reactor. Further, a settling plate 6 at the top of the Stage II reactor further minimizes carryover of solids into the Stage III reactor. This settling plate can be any commercially available (e.g., tube settlers, settling plates). The Applicant's proprietary horizontal plate microbial support media 20, shown in FIGS. 4 and 5, modified to serve as a settling surface, is the preferred settling plate.

The Stage II fluidized bed is biologically active, entrapping suspended and colloidal solids, and completing the hydrolysis phase by metabolizing the remaining fine suspended and colloidal solids from Stage I, and continuing the acidification phase. Gases released in the Stage II reactor 5, collected at a second raw gas outlet, consisting primarily of carbon dioxide ($CO_2$) and hydrogen ($H_2$), are piped to the Stage III reactor 10 via a raw gas collection system (e.g., upper conduit 11). The overflow effluent (filtered supernatant) from Stage II exits via a liquid outlet and is then pumped to the base of Stage III (at a liquid inlet) via the overflow (second) conduit 7.

While being pumped from Stage II to Stage III (via the lower conduit 7 to the third digestion tank inlet), the filtered supernatant flows through a heater means (e.g., heat exchanger) 8 to raise the temperature to 30° to 38° C. (85° to 100° F.), the optimum temperature for mesophilic operation, or 49° to 57° C. (120° to 135° F.), the optimum temperature for thermophilic operation (preferred). At this time, the pH of the Stage II supernatant is also adjusted to 7.8 to 8.5 (optimum pH for methane production) via a pH adjusting means (e.g., in-line pH probes, automated, computer-controlled chemical feed pumps, static mixer 9).

Stage III is a packed bed (fixed film) reactor 10 (the "third" digestion tank). The packing material can be various types of random or vertical sheet media, including cross-flow or tubular media. However, for optimization of methane production, the preferred media is the applicant's proprietary horizontal plate microbial support media 20 (shown in FIGS. 4 and 5).

It is preferred that two different zones be created within the Stage III reactor 10, namely an upper media bed portion 16 and a lower media bed portion 15. The lower portion of the Stage III reactor preferably containing high angle anaerobic digester media, the height or extent varying with the specific application. The angle will be variable, but the preferred angle is 60 degrees from the horizontal.

The upper portion of the Stage III reactor contains a second digester media, preferably contains low angle anaerobic digester media, the height or extent varying with the specific application. The angle will be variable but the preferred angle is 45 degrees from the horizontal. This use of a reduced angle increases the available surface area for attachment of the methanogen community. Alternatively, applicant's proprietary horizontal plate microbial support enhanced surface area media (shown in FIGS. 4 and 5) can be applied in the upper media bed to increase surface area.

The preferred horizontal plate anaerobic digester media in Stage III is used to combine hydraulic and biological characteristics which maximize methane production. Hydraulically, the anaerobic digester media induces constant mixing, remixing, and flow splitting at low upflow velocities to insure maximum contact of the liquid-borne substrates with the microbial community attached to the media. Biologically, the anaerobic digester horizontal media provides a microbial film on the upper impingement surface to ensure agglomeration and capture of residual colloidal solids. These agglomerated particles then drop to the lower surface of the media where the final acidification and acetogenesis and takes place, forming water soluble acetate, and other water soluble organics suitable as food for methanogens. This media permits the additional development of multiple phases in the Stage III reactor 10.

The methane bacteria permanently attach to the upper surface of the anaerobic digester media where they have maximum exposure to food and are isolated from direct ecological competition with residual hydrolysis and acidogenesis microorganisms on the lower surface. The provision of a solid and permanent attachment surface for the methanogens prevents loss (washout) of these slow growing microorganisms, maximizing the stability and energy productivity of the system.

The raw gas (carbon dioxide ($CO_2$) and hydrogen ($H_2$)) from Stages I and II (carried via the upper conduit 11 (raw gas collection system)) preferably enter the Stage III reactor at the base of the upper media bed (at the raw gas inlet). This configuration protects the acetogenic phase microorganism in the lower media bed from elevated concentrations of hydrogen gas which could limit their activity and the production of acetate, an important food source for the methanogenic microorganisms. The carbon dioxide ($CO_2$) and hydrogen ($H_2$) gases from Stages I and II, as they move upward through the upper media bed, provide an additional food source for the attached methane-producing microorganisms, thereby reducing the carbon dioxide ($CO_2$) in the final biogas product.

During the Stage I active mixing phase, when no new feedstock is being pumped into Stage III, supernatant will recirculate from the top to bottom (piping not shown in FIG. 1) of Phase III to ensure stable pH and temperature and more complete uptake of substrate and production of methane. However, the entire process can be operated as either a continual flow process or a semi-continual flow process.

When new feedstock is pumped into Stage I, a like amount of liquid (filtered effluent) will preferably exit Stage III via a discharge conduit (effluent outlet) 12. Due to contact in the fluidized bed of Stage II and the packed bed of Stage III, this discharge liquid will require relatively little additional treatment prior to discharge (e.g., application to land (irrigation)).

Methane gas ($CH_4$), produced in Stage III, is piped off the top of the Stage III reactor via a methane outlet (gas conduit) 13 where it is collected and stored.

It is preferred that flocculant (e.g., ferric chloride ($FeCl_3$)) be added to the supernatant, for instance at call out 17 in FIG. 1. The purpose of the flocculant being to assist in the flocculation and/or precipitation of phosphorus from the supernatant, thereby decreasing the formation of mineral deposits, such as struvite (ammonium magnesium phosphate) within the second and third digester tanks and associated equipment.

While the preferred location of injection of the ferric chloride is before Stage II, it could be injected at Stage I or before both Stages I and II.

There are a number of benefits to various embodiments of the present invention. First, the hydrolysis and acidification phases are separated from the methanogenic phase through a three-stage process based on particle size, particle density, and intermediate product solubility factors. This reduces the potential for process failure and increases the rate of energy production. The methanogens in Stage III are protected from changes in pH, temperature and the effect of toxins and/or heavy metals that exist in the earlier stages and are provided with ideal conditions of pH and temperature to optimize energy production. The methanogens in Stage III are provided with ideal environmental conditions to maximize methane gas production.

Second, the quantity and cost of pH control chemicals is significantly reduced because pH control is only required in the smaller Stage III tank. As a result, the system permits automated, computer-controlled monitoring and adjustment to the optimum pH levels required for methane production. This also reduces operator attention requirements and the possibility of operator error. In Stage I, allowance of a lower pH increases the rate of particulate size reduction and microbial hydrolysis, thereby further benefiting the efficiency of the system. The reduced demand for pH adjusting chemicals also permits economical use of sodium bicarbonate as a preferred pH control chemical in Stage III.

Third, maintaining thermophilic temperatures in Stage III is the preferred mode of operation. The present anaerobic digester system significantly reduces heating requirements associated with conventional thermophilic digestion in that only the smaller Stage III reactor(s) are heated to the thermophilic temperatures (49° to 57° C.) required for increased methane ($CH_4$) production. The present anaerobic digester system also eliminates odor and waste solids dewatering problems associated with conventional thermophilic operations. The waste sludges from Stage I, which operates at lower temperatures, do not exhibit the increased odor formation and poor dewatering characteristics associated with conventional single-stage anaerobic digesters operated at thermophilic temperatures.

Fourth, there is a significant reduction of loss (washout) of methanogens due to provision of permanent attachment media sites in the Stage III reactor for the methanogens to attach to, increasing process stability and energy production rates.

Fifth, Applicant's anaerobic digester system utilizes stock equipment (e.g., tanks, chopper pumps, mixers, heat exchangers, solids handling equipment, pH and temperature adjustment monitors and controls), further increasing process reliability.

Sixth, the anaerobic digester system significantly reduces operational and operator skill requirements due to semi-automatic operation. Operators are still required for feeding solids (feedstock) into the Stage I reactor and removing digested sludge, but operator requirements for estimating and adjusting pH and temperature are eliminated.

Seventh, methane ($CH_4$) gas produced by the Stage III reactor will be of a significantly higher BTU content with less carbon dioxide ($CO_2$) than that produced from conventional digesters. This is due to the method of piping carbon dioxide ($CO_2$) and hydrogen ($H_2$) gases produced in Stages I and II to the Stage III fixed film reactor which will increase conversion of these gases to methane ($CH_4$).

Eighth, the present anaerobic digester system will permit increased rates of solids digestion in Stage I, will improve waste solids dewatering characteristics, will reduce odors, and will reduce final disposal requirements and costs.

Ninth, the invented anaerobic digester system can be both applied to new construction and used to retrofit pre-existing anaerobic digester (single stage) systems to improve energy production rates in the latter.

Tenth, due to the combination of design factors in the anaerobic digester system, including separation of phases, use of the horizontal microbial attachment media, reduced heating requirement for thermophilic operation, increased stability at thermophilic temperatures, and reduced potential for operator error and operator skill levels, embodiments of the invented anaerobic digester three stage system should at least double, and potentially triple, the net energy output as compared to conventional single tank designs.

Figure 3:
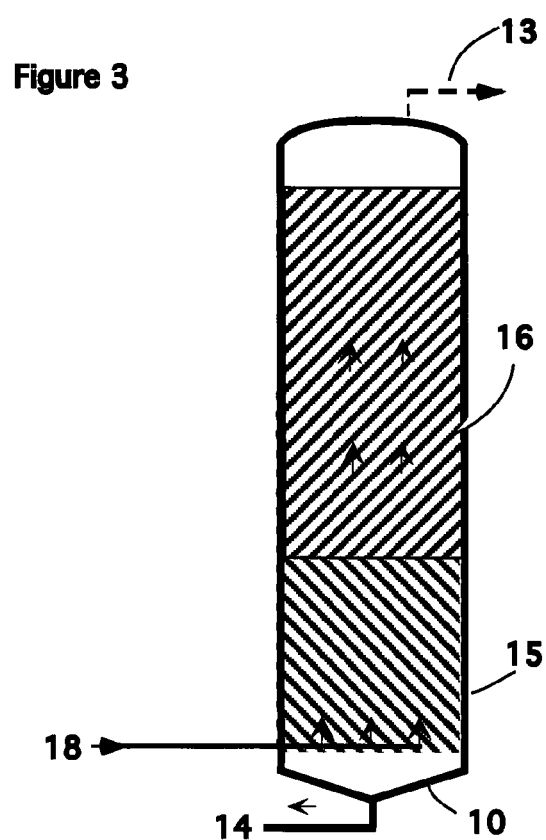
FIG. 3 is a partial schematic representation of a fourth embodiment of a three stage, multiple phase anaerobic digestion system.

Referring now to FIG. 3, shown is an alternative embodiment of a Stage III rector. Since carbon dioxide ($CO_2$) is a food source for methane producing bacteria, Stage III can also be used as a unique reactor (without Stages I and II) to biologically transform carbon dioxide ($CO_2$) from stack gases and other point sources of carbon dioxide ($CO_2$) entering the atmosphere into methane ($CH_4$) gas which can be used as a fuel. In the case of stack gases, the air stream 18 carrying the $CO_2$ and other pollutants will preferably be first combined into a liquid carrier (e.g., water, wastewater), possibly under slight pressure, and then be pumped through Stage III to transform the $CO_2$ into methane ($CH_4$) gas.

Example implementation. Injecting raw feedstock into a primary digestion tank; mixing the contents of the primary digestion tank mechanically, thereby reducing the size of the raw organic solids contained in the feedstock; holding feedstock in the digestion tank for a predetermined period of time to provide for extensive but incomplete microbial hydrolysis; ceasing mixing to allow for settling of denser solids; drawing off a supernatant from the upper portion of the contents of the primary digestion tank; pumping said supernatant to a second digestion tank; collecting gases from the first digestion tank and transmitting said gasses to the base of a third digestion tank; draining undigested material from the bottom of the first digestion tank; maintaining the first digestion tank and second digestion tank at a temperature of 24° C. to 35° C.; operating the second digestion tank as an upflow fluidized bed reactor; adjusting upflow velocity to that which will minimize overflow of the suspended solids to the third digestion tank; utilizing a settling plate at the top of the second digestion tank to minimize carryover of solids into the third digestion tank; collecting gases from the second digestion tank and transmitting said gases to the base of the third digestion tank; pumping effluent from the second digestion tank to the base of the third digestion tank; heating said supernatant to a temperature of 30° to 38° C. or 49° to 57° C. before injection into said third digestion tank; adjusting the pH of the supernatant to 7.8 to 8.5 using in-line pH probes, automated, computer-controlled chemical feed pumps and a static mixer before injection into the third digestion tank; operating said third digestion tank as a packed bed (fixed film) reactor; creating two different zones within the third digestion tank, namely an upper portion containing low angle or enhanced surface area anaerobic digester media and a lower portion containing high angle anaerobic digester media; utilizing gases from the first and second digestion tanks in the third digestion tank as an additional food source for the attached methane producing microorganisms; discharging liquid from said third digestion tank generally equal to the amount of new feedstock pumped into said first digestion tank; and collecting and storing methane gas produced in said third digestion tank.

First example embodiment. A method for the anaerobic digestion of a raw feedstock containing raw organic solids, said method comprising: transferring a quantity of said feedstock into a first digestion tank; mixing and chopping said feedstock to reduce the size of the raw organic solids contained in said feedstock; holding said feedstock in said first digestion tank for a predetermined period of time to provide for at least partial microbial hydrolysis of said feedstock, wherein said feedstock has a pH of 5.5 to 6.5; ceasing the mixing of said feedstock and allowing the settling of solids from a supernatant; drawing off a portion of said supernatant from said first digestion tank and transferring said drawn off portion to a second digestion tank; collecting first gases from said first digestion tank and transmitting said first gasses to a third digestion tank; maintaining the temperature of said supernatant in said first digestion tank between 24° C. to 35° C.; operating said second digestion tank as an upflow fluidized bed reactor, said reactor having a top and a bottom, wherein supernatant pumped from said first digestion tank enters said second digestion tank at said bottom and exits said second digestion tank at said top as filtered supernatant, wherein said feedstock has a pH of 5.5 to 6.5; adjusting the upflow velocity of the supernatant moving through said second digestion tank to minimize suspended and colloidal solids in said filtered supernatant; drawing off a second portion of said filtered supernatant from said second digestion tank; collecting second gases from said second digestion tank and transmitting said second gases to said third digestion tank; maintaining the temperature of said supernatant in said second digestion tank between 24° C. to 35° C.; heating said filtered supernatant to a mesophilic temperature or a thermophilic temperature; adjusting the pH of the filtered supernatant to maintain a pH of 7.8 to 8.5 in said third digestion tank; transferring said second portion of filtered supernatant to said third digestion tank; operating said third digestion tank as a packed bed reactor having an upper portion containing a second digester media, where the second digester media is selected from the group consisting of low angle anaerobic digester media and enhanced surface area media, and a lower portion containing high angle anaerobic digester media, said filtered supernatant flowing through said lower portion then through said upper portion; injecting said first and second gasses into said third digestion tank upper portion; discharging filtered effluent from said third digestion tank; and collecting and storing methane gas produced in said third digestion tank.

Second example embodiment. A three stage, multiple phase anaerobic digestion system for the anaerobic digestion of a feedstock, said system comprising: a first digestion tank in which the hydrolysis of said feedstock begins, said first digestion tank having a top and a bottom, said first digestion tank including a mixing means for mixing said feedstock, said first digestion tank having a gas outlet adjacent said top for allowing gasses within said first digestion tank to be collected, and a liquid outlet adjacent said top for allowing a supernatant to be removed from said first digestion tank; a first conduit connecting said first digestion tank liquid outlet to a second digestion tank inlet thereby allowing said supernatant to be conveyed from said first digestion tank to said second digestion tank; a second digestion tank in which the hydrolysis of said feedstock completes and the acidogenesis of said feedstock takes place, said second digestion tank having a top and a bottom, said second digestion tank operated as an upflow fluidized bed reactor, said second digestion tank including said second digestion tank inlet adjacent said bottom, a gas outlet adjacent said top for allowing gasses within said second digestion tank to be collected, and a liquid outlet adjacent said top for allowing a filtered supernatant to be removed from said second digestion tank; a second conduit connecting said second digestion tank liquid outlet to a third digestion tank inlet thereby allowing said filtered supernatant to be conveyed from said second digestion tank to said third digestion tank; a heater means connecting with said second conduit; a pH adjusting means connecting with said second conduit, said pH adjusting means for adjusting the pH of the filtered supernatant to 7.8 to 8.5; a third digestion tank in which the methanogenesis of said feedstock takes place, said third digestion tank having a top and a bottom, said third digestion tank including said third digestion tank inlet adjacent said bottom, a methane outlet adjacent said top for allowing methane within said third digestion tank to be collected, and a liquid outlet adjacent said top for allowing a filtered effluent to be removed from said third digestion tank, wherein said third digestion tank is operated as a packed bed reactor, said third digestion tank comprising an upper portion containing a second digester media, where the second digester media is selected from the group consisting of low angle anaerobic digester media and enhanced surface area media, and a lower portion containing high angle anaerobic digester media, said third digestion tank further comprising a raw gas inlet above said high angle anaerobic digester media but below said low angle anaerobic digester media for injection of raw gas into said upper portion; and a raw gas collection system connecting said first and second digestion tank gas outlets with said third digestion tank's raw gas inlet.

Third example embodiment. A system for the anaerobic digestion of a raw feedstock containing raw organic solids, said system comprising: a hydrolysis tank where partial hydrolysis of the feedstock takes place, wherein the pH of the feedstock in said hydrolysis tank has a pH of 5.5 to 6.5, wherein the temperature of said feedstock in said hydrolysis tank is maintained between 24° C. to 35° C., wherein after a predetermined period of time, supernatant is drawn off said hydrolysis tank, wherein carbon dioxide ($CO_2$) and hydrogen gas ($H_2$) formed in said hydrolysis tank are collected; an upflow fluidized bed reactor having a top and a bottom, said bottom for receiving the drawn off supernatant from said hydrolysis tank, said upflow fluidized bed reactor providing for hydrolysis and acidogenesis of said supernatant, wherein the pH of the supernatant in said upflow fluidized bed reactor has a pH of 5.5 to 6.5, wherein the temperature of said supernatant in said upflow fluidized bed reactor is maintained between 24° C. to 35° C., wherein said supernatant exists said upflow fluidized bed reactor at said top as filtered supernatant, wherein carbon dioxide ($CO_2$) and hydrogen gas ($H_2$) formed in said upflow fluidized bed reactor are collected; a heating means for heating said filtered supernatant to at least 30° C.; a pH adjusting means for adjusting the pH of the filtered supernatant to maintain a pH of 7.8 to 8.5 in said third digestion tank; and a packed bed reactor where methanogenic bacteria create methane, said packed bed reactor having an inlet end and an outlet end, wherein said filtered supernatant is transferred into said packed bed reactor at or adjacent said inlet end, wherein said packed bed reactor includes a biological filter media, wherein said carbon dioxide ($CO_2$) and hydrogen gas ($H_2$) collected from said hydrolysis tank and said upflow fluidized bed reactor are injected into said filtered supernatant within said packed bed reactor, said filtered supernatant, said injected carbon dioxide ($CO_2$) and said injected hydrogen gas ($H_2$) for digestion by said methanogenic bacteria, said packed bed reactor having a discharge port through which filtered effluent is discharged from said packed bed reactor, wherein methane gas ($CH_4$) produced in said packed bed reactor is drawn off and stored.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

The purpose of the Abstract is to enable the public, and especially the scientists, engineers, and practitioners in the art who are not familiar with patent or legal terms or phraseology, to determine quickly from a cursory inspection, the nature and essence of the technical disclosure of the application. The Abstract is neither intended to define the invention of the application, which is measured by the claims, nor is it intended to be limiting as to the scope of the invention in any way.

Still other features and advantages of the claimed invention will become readily apparent to those skilled in this art from the following detailed description describing preferred embodiments of the invention, simply by way of illustration of the best mode contemplated by carrying out my invention. As will be realized, the invention is capable of modification in various obvious respects all without departing from the invention. Accordingly, the drawings and description of the preferred embodiments are to be regarded as illustrative in nature, and not as restrictive in nature.

I claim:

1. A method for the anaerobic digestion of a raw feedstock containing raw organic solids, said method comprising:
    transferring a quantity of said feedstock into a first digestion tank;
    mixing and chopping said feedstock to reduce the size of the raw organic solids contained in said feedstock;
    holding said feedstock in said first digestion tank for a predetermined period of time to provide for at least partial microbial hydrolysis of said feedstock, wherein said feedstock has a pH of 5.5 to 6.5;
    ceasing the mixing of said feedstock and allowing the settling of solids from a supernatant;
    drawing off a portion of said supernatant from said first digestion tank and transferring said drawn off portion to a second digestion tank;
    collecting first gases from said first digestion tank and transmitting said first gasses to a third digestion tank;
    maintaining the temperature of said supernatant in said first digestion tank between 24° C. to 35° C.;
    operating said second digestion tank as an upflow fluidized bed reactor, said reactor having a top and a bottom, wherein supernatant pumped from said first digestion tank enters said second digestion tank at said bottom and exits said second digestion tank at said top as filtered supernatant, wherein said feedstock has a pH of 5.5 to 6.5;
    adjusting the upflow velocity of the supernatant moving through said second digestion tank to minimize suspended and colloidal solids in said filtered supernatant;
    drawing off a second portion of said filtered supernatant from said second digestion tank;
    collecting second gases from said second digestion tank and transmitting said second gases to said third digestion tank;
    maintaining the temperature of said supernatant in said second digestion tank between 24° C. to 35° C.;
    heating said filtered supernatant to a mesophilic temperature or a thermophilic temperature;

adjusting the pH of the filtered supernatant to maintain a pH of 7.8 to 8.5 in said third digestion tank;

transferring said second portion of filtered supernatant to said third digestion tank;

operating said third digestion tank as a packed bed reactor having an upper portion containing a second digester media, where the second digester media is selected from the group consisting of low angle anaerobic digester media and enhanced surface area media, and a lower portion containing high angle anaerobic digester media, said filtered supernatant flowing through said lower portion then through said upper portion;

injecting said first and second gasses into said third digestion tank upper portion;

discharging filtered effluent from said third digestion tank; and collecting and storing methane gas produced in said third digestion tank.

2. The method of claim 1, wherein the volume of the discharged filtered effluent is generally equal to the amount of new feedstock pumped into said first digestion tank.

3. The method of claim 1, wherein said mesophilic temperature is 30° C. to 38° C.

4. The method of claim 1, wherein said thermophilic temperature is 49° C. to 57° C.

5. The method of claim 1, further comprising the step of draining said solids from said first, second and third digestion tanks.

6. The method of claim 1, further comprising the step of utilizing a settling plate at the top of said second digestion tank to minimize carryover of suspended and colloidal solids in said filtered supernatant.

7. The method of claim 1, further comprising the step of removing settled solids from said first, second and third digestion tanks.

8. A three stage, multiple phase anaerobic digestion system for the anaerobic digestion of a feedstock, said system comprising:

a first digestion tank in which the hydrolysis of said feedstock begins, said first digestion tank having a top and a bottom, said first digestion tank including a mixing means, wherein the mixing means is configured for mixing said feedstock, said first digestion tank having a gas outlet adjacent said top for allowing gasses within said first digestion tank to be collected, and a liquid outlet adjacent said top for allowing a supernatant to be removed from said first digestion tank;

a first conduit connecting said first digestion tank liquid outlet to a second digestion tank inlet thereby allowing said supernatant to be conveyed from said first digestion tank to said second digestion tank;

a second digestion tank in which the hydrolysis of said feedstock completes and the acidogenesis of said feedstock takes place, said second digestion tank having a top and a bottom, said second digestion tank operated as an upflow fluidized bed reactor, said second digestion tank including said second digestion tank inlet adjacent said bottom, a gas outlet adjacent said top for allowing gasses within said second digestion tank to be collected, and a liquid outlet adjacent said top for allowing a filtered supernatant to be removed from said second digestion tank;

a second conduit connecting said second digestion tank liquid outlet to a third digestion tank inlet thereby allowing said filtered supernatant to be conveyed from said second digestion tank to said third digestion tank;

a heater means, wherein the heater means is configured for connecting with said second conduit;

a pH adjusting means, wherein the pH adjusting means is configured for connecting with said second conduit, said pH adjusting means is configured for adjusting the pH of the filtered supernatant to 7.8 to 8.5;

a third digestion tank in which the methanogenesis of said feedstock takes place, said third digestion tank having a top and a bottom, said third digestion tank including said third digestion tank inlet adjacent said bottom, a methane outlet adjacent said top for allowing methane gas within said third digestion tank to be collected, and a liquid outlet adjacent said top for allowing a filtered effluent to be removed from said third digestion tank, wherein said third digestion tank is operated as a packed bed reactor, said third digestion tank comprising an upper portion and a lower portion, said upper portion containing digester media selected from the group consisting of low angle anaerobic digester media and enhanced surface area media, and said lower portion containing high angle anaerobic digester media, said third digestion tank further comprising a raw gas inlet above said high angle anaerobic digester media but below said low angle anaerobic digester media for injection of raw gas into said upper portion; and a raw gas collection system connecting said first and second digestion tank gas outlets with said third digestion tank's raw gas inlet.

9. The three stage, multiple phase anaerobic digestion system of claim 8, wherein said heater means heats said filtered supernatant to a temperature of 30° to 38° C.

10. The three stage, multiple phase anaerobic digestion system of claim 8, wherein said heater means heats said filtered supernatant to a temperature of 49° to 57° C.

11. The three stage, multiple phase anaerobic digestion system of claim 8, wherein said feedstock is held within the first digestion tank for a predetermined period of time to provide for extensive but incomplete microbial hydrolysis.

12. The three stage, multiple phase anaerobic digestion system of claim 8, wherein said first digestion tank and said second digestion tank are maintained at a temperature of 24° C. to 35° C.

13. The three stage, multiple phase anaerobic digestion system of claim 8, wherein said second digestion tank comprises a settling plate at the top of the second digestion tank to minimize carryover of solids into the third digestion tank.

14. The three stage, multiple phase anaerobic digestion system of claim 8, wherein a volume of filtered effluent is discharged from said third digestion tank generally equal to the amount of new feedstock pumped into said first digestion tank.

15. The three stage, multiple phase anaerobic digestion system of claim 8, wherein the methane gas produced in said third digestion tank is collected and stored.

16. A system for the anaerobic digestion of a raw feedstock containing raw organic solids, said system comprising:

a hydrolysis tank where partial hydrolysis of the feedstock takes place, wherein the pH of the feedstock in said hydrolysis tank has a pH of 5.5 to 6.5, wherein the temperature of said feedstock in said hydrolysis tank is maintained between 24° C. to 35° C., wherein after a predetermined period of time, supernatant is drawn off said hydrolysis tank, wherein carbon dioxide ($CO_2$) and hydrogen gas ($H_2$) formed in said hydrolysis tank are collected via a raw gas collection system;

an upflow fluidized bed reactor having a top and a bottom, said bottom for receiving the drawn off supernatant from said hydrolysis tank, said upflow fluidized bed reactor providing for hydrolysis and acidogenesis of said supernatant, wherein the pH of the supernatant in said upflow fluidized bed reactor has a pH of 5.5 to 6.5, wherein the temperature of said supernatant in said upflow fluidized bed reactor is maintained between 24° C. to 35° C., wherein said supernatant exists said upflow fluidized bed reactor at said top as filtered supernatant, wherein carbon dioxide ($CO_2$) and hydrogen gas ($H_2$) formed in said upflow fluidized bed reactor are collected via said raw gas collection system;

a heating means, wherein the mixing means is configured for heating said filtered supernatant to at least 30° C.;

a pH adjusting means, wherein the pH adjusting means is configured for adjusting the pH of the filtered supernatant to maintain a pH of 7.8 to 8.5 in said third digestion tank;

a packed bed reactor where methanogenic bacteria create methane, said packed bed reactor having an inlet end and an outlet end, wherein said filtered supernatant is transferred into said packed bed reactor at or adjacent said inlet end, wherein said packed bed reactor includes a biological filter media, wherein said carbon dioxide ($CO_2$) and hydrogen gas ($H_2$) collected by said raw gas collection system from said hydrolysis tank and said upflow fluidized bed reactor are injected into said filtered supernatant within said packed bed reactor, said filtered supernatant, said injected carbon dioxide ($CO_2$) and said injected hydrogen gas ($H_2$) for digestion by said methanogenic bacteria, said packed bed reactor having a discharge port through which filtered effluent is discharged from said packed bed reactor, wherein methane gas ($CH_4$) produced in said packed bed reactor is drawn off and stored;

said raw gas collection system fluidly connecting said hydrolysis tank and said upflow fluidized bed reactor to said packed bed reactor; and wherein said packed bed reactor has an upper portion containing low angle anaerobic digester media and a lower portion containing high angle anaerobic digester media, wherein said filtered supernatant flowing through said lower portion then through said upper portion.

17. The system of claim 16, wherein said heating means heats said filtered supernatant to a temperature of 30° to 38° C.

18. The system of claim 16, wherein said heating means heats said filtered supernatant to a temperature of 49° to 57° C.

19. The system of claim 16, wherein said gasses are injected into said filtered supernatant within said packed bed reactor at a location spaced from said inlet end of said reactor.

* * * * *

UNITED STATES PATENT AND TRADEMARK OFFICE
CERTIFICATE OF CORRECTION

| | | |
|---|---|---|
| PATENT NO. | : 8,765,449 B2 | Page 1 of 1 |
| APPLICATION NO. | : 13/056841 | |
| DATED | : July 1, 2014 | |
| INVENTOR(S) | : Stewart | |

It is certified that error appears in the above-identified patent and that said Letters Patent is hereby corrected as shown below:

In the Claims

Claim 16, col. 15, line 7, change "exists" to "exits".

Claim 16, col. 15, line 12, change "mixing" to "heating".

Claim 16, col. 15, lines 16-17, change "said third digestion tank" to "a packed bed reactor".

Claim 16, col. 15, line 18, replace "a" with "said".

Signed and Sealed this
Seventh Day of October, 2014

Michelle K. Lee
*Deputy Director of the United States Patent and Trademark Office*